(12) United States Patent
Yu

(10) Patent No.: US 8,080,047 B2
(45) Date of Patent: Dec. 20, 2011

(54) LIGHT THERAPY DEVICE

(75) Inventor: Chu Yih Yu, San Chung (TW)

(73) Assignee: Mesure Technology Co., Ltd., San Chung, Taipei Hsien (TW)

( * ) Notice: Subject to any disclaimer, the term of this patent is extended or adjusted under 35 U.S.C. 154(b) by 707 days.

(21) Appl. No.: 11/461,489

(22) Filed: Aug. 1, 2006

(65) Prior Publication Data

US 2008/0033512 A1 Feb. 7, 2008

(51) Int. Cl.
*A61N 5/06* (2006.01)
(52) U.S. Cl. ........... 607/93; 606/2; 606/3; 606/14; 607/88
(58) Field of Classification Search .......... None
See application file for complete search history.

(56) References Cited

U.S. PATENT DOCUMENTS

| 5,683,436 | A * | 11/1997 | Mendes et al. ........... 607/88 |
| 6,583,447 | B2 * | 6/2003 | Wang et al. ........... 257/99 |
| 2006/0167531 | A1 * | 7/2006 | Gertner et al. ........... 607/86 |

* cited by examiner

*Primary Examiner* — Henry M Johnson, III
*Assistant Examiner* — Lynsey Crandall
(74) *Attorney, Agent, or Firm* — Thomas, Kayden, Horstemeyer & Risley, LLP

(57) ABSTRACT

A light therapy device for rhinitis treatment. The light therapy device includes a hollow tube body with a longitudinal axis, being dimensioned and configured to permit insertion into a nostril of a treatment subject. A light emitting diode package disposed within the hollow tube body includes a first LED chip as a red light source and a second LED chip as an infrared light source. The first LED chip and the second LED chip are at different plane substantially orthogonal to the longitudinal axis.

5 Claims, 4 Drawing Sheets

1

LIGHT THERAPY DEVICE

BACKGROUND OF THE INVENTION

The invention relates to the field of light therapy devices. More particularly, the invention relates to the field of light therapy devices for treating rhinitis.

U.S. Pat. No. 5,683,436 discloses a traditional light therapy device design which affords low cost apparatus for treating rhinitis by producing a non-coherent source of illumination. The exact wavelength of the illumination is confined to a relatively narrow bandwidth (+/−25 nm) centered at a wavelength which may be predetermined and provided by suitable selection of LED packages in LED pack. Experimental evidence indicates that red light, particularly 660 nm light, is particularly suitable for the treatment of rhinitis. However, the diameter of the LED pack may be too large to be inserted into the patient's nostril since the LED packages of the LED pack are disposed on a same plane and each LED package only contains a LED chip. Furthermore, R.O.C. Utility Model Pat. No. 271586 discloses another traditional light therapy device design which affords a hollow tube body with a narrower upper portion and a wider lower portion. The narrower upper portion permits insertion into a patient's nostril and a red light LED and an infrared light LED are disposed at the wider lower portion to solve the above-described problem. However, their light intensity may be attenuated since the LEDs are away from the front end of the hollow tube body.

SUMMARY OF THE INVENTION

An exemplary embodiment of the present invention overcomes the above-described problems by providing a light therapy device for treating rhinitis. The light therapy device comprises a control unit and a hollow tube body with a longitudinal axis. The hollow tube body is dimensioned and configured to permit insertion into a nostril of a treatment subject, and a light emitting diode package is disposed within the hollow tube body. The light emitting diode package comprises a first LED chip as a first light source and a second LED chip as a second light source, controlled by the control unit. The first LED chip and the second LED chip are at different plane substantially orthogonal to the longitudinal axis.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF THE INVENTION

Various aspects of the system and method of the present invention will be described, and for purposes of explanation, specific configurations and details are set forth in order to provide a thorough understanding of the present invention. However, it will be apparent to one skilled in the art that the present invention may be practiced without these specific details. Furthermore, well known features have been omitted or simplified in order to prevent obscuring the present invention.

Figure 1:
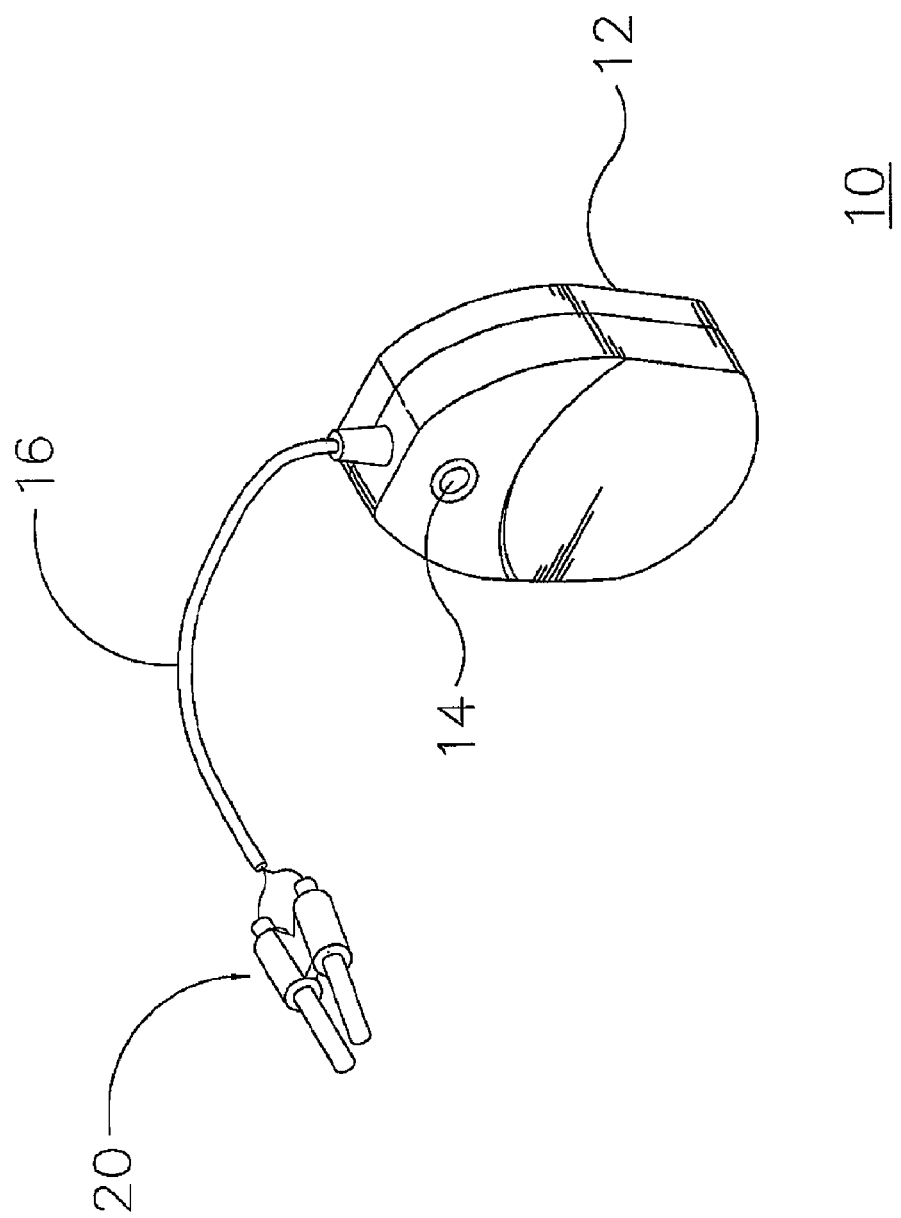
FIG. 1 is a schematic illustration of a light therapy device according to an exemplary embodiment of the present invention.

FIG. 1 illustrates a light therapy device 10 for treating rhinitis such as a runny nose or an itchy nose, according to an exemplary embodiment of the present invention. The light therapy device 10 includes a control unit 12 and a hollow tube structure 20 electrical connecting thereto via wires 16. Specifically, the control unit 12 also includes a switch 14 to turn on and off the hollow tube structure 20. In general, the hollow tube structure 20 may include a pair of hollow tube portions, preferably, composed of transparent material such as glass or polymethyl methacrylate (PMMA).

Figure 2:
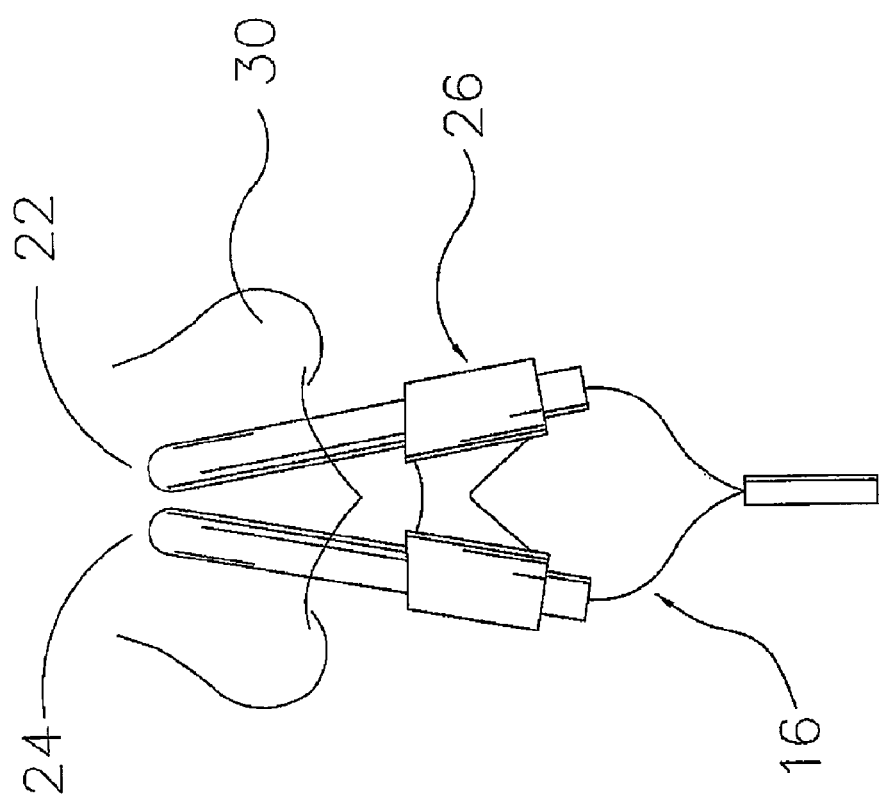
FIG. 2 is a schematic illustration of a light therapy device for treating rhinitis according to an exemplary embodiment of the present invention.

For example, turning now to FIG. 2, a pair of hollow tube portions 22 and 24 are dimensioned and configured to permit insertion into a pair of nostrils 30 of a treatment subject such as a patient. In this case, light therapy device 10 may further comprise a pair of holders 26 sized to receive the pair of hollow tube portions 22 and 24 for clamping the pair of hollow tube portions 22 and 24 to the pair of nostrils 30.

Figure 3:
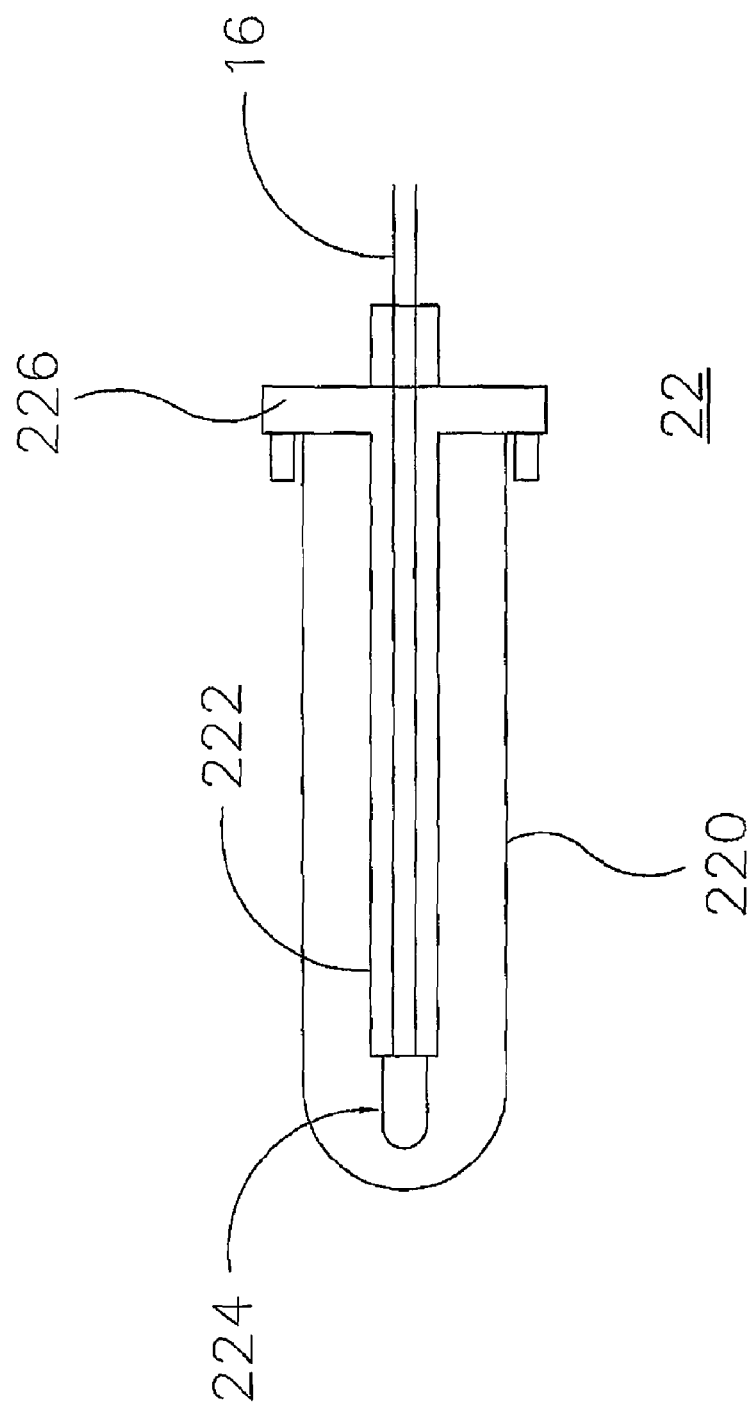
FIG. 3 is a cross-sectional view of a hollow tube body of the light therapy device of FIG. 2 according to an exemplary embodiment of the present invention.

Referring to FIG. 3, hollow tube portion 22 comprises a hollow tube body 220 and a light emitting diode package 224 is disposed within the hollow tube body 220. Furthermore, an inner support tube body 222 can be adapted for supporting the light emitting diode package 224. In one example, the inner support tube body 222 is opaque for avoiding the wires 16 being exposed, since the wires 16 pass through the inner support tube body 222.

In a preferred embodiment, inner support tube body 222 is disposed within the hollow tube body 220 for supporting the light emitting diode package 224, and a wider bottom portion 226 extends from the inner support tube body 222. In this case, the hollow tube body 220 can be securely inserted into the wider bottom portion 226 in a detachable form.

Figure 4:
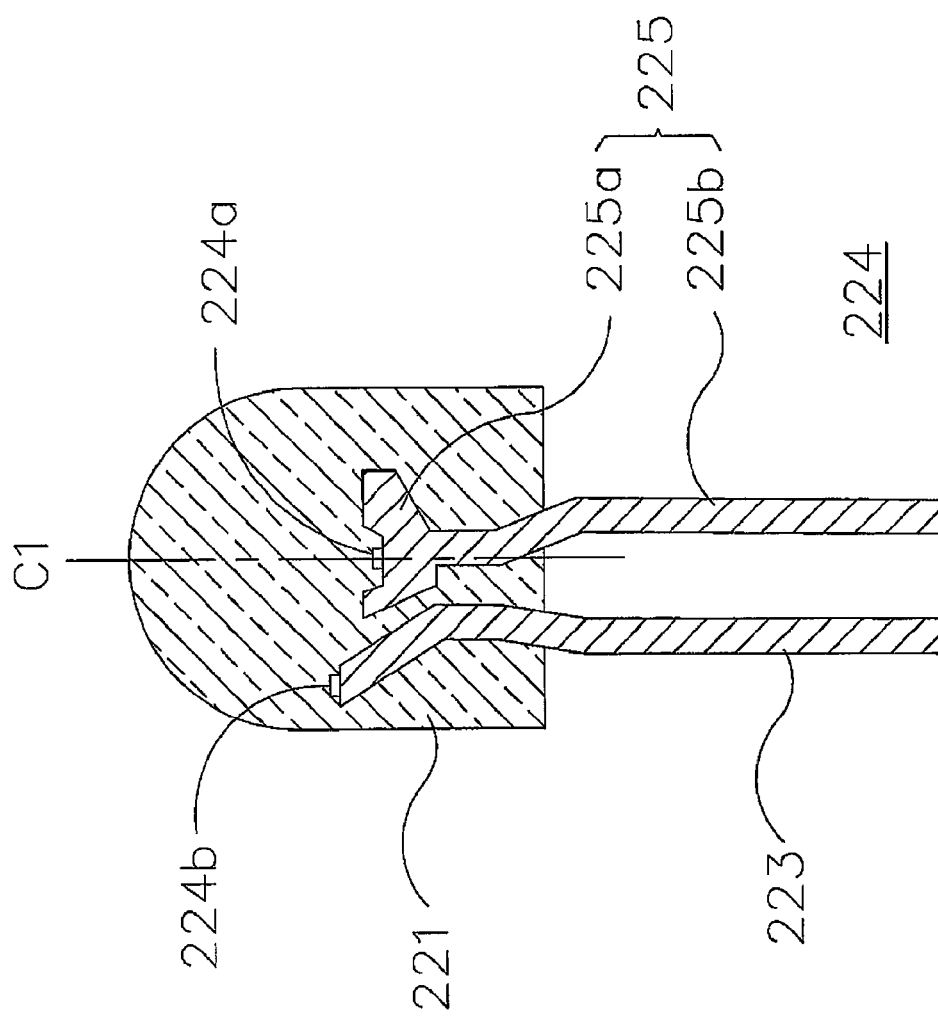
FIG. 4 shows LED chips in a LED package of FIG. 3 according to an exemplary embodiment of the present invention.

Next, referring to FIG. 4, as a main feature and a key aspect of an exemplary embodiment of the invention, a light emitting diode package 224 comprises a first LED chip 224a as a first light source controlled by the control unit 12, emitting non-coherent light radiation having a narrow band-width centered at a red light wavelength suitable for rhinitis treatment; and a second LED chip 224b as a second light source controlled by the control unit 12, emitting non-coherent light radiation having a narrow band-width centered at an infrared light wavelength suitable for heating the hollow tube body 220. Specifically, the first LED chip 224a and the second LED chip 224b are at different plane substantially orthogonal to the longitudinal axis C1 of the hollow tube body 220.

The first LED chip 224a is typically and preferably located along the longitudinal axis C1 of the hollow tube body 220 since its emitting light property is narrow band-width centered at a red light wavelength such as in a range of about 630 nm to about 660 nm, preferably about 652 nm, suitable for rhinitis treatment. On the other hand, the second LED chip 224b with infrared light wavelength is typically and preferably located a predetermined distance away from the longitudinal axis C1 thereof, namely more near the sidewall of the hollow tube body 220 for easily heating. The infrared light wavelength is typically in a range of about 920 nm to about 960 nm, preferably about 940 nm.

In a most preferred embodiment, the light emitting diode package 224 that can be powered and controlled, via wires 16, by the control unit 12, may further comprise a first mount lead 225 for mounting the first LED chip 224a; and a second mount lead 223 disposed slightly away from the first mount lead 225, for mounting the second LED chip 224b. In one example, the first mount lead 225 and the second mount lead 223 respectively electrically connect the wires 16.

Typically, the first mount lead 225 may comprise a cup 225a for accommodating the first LED chip 224a and a lead 225b for supporting the cup 225a. And the preferred second mount lead 223 may comprise an end surface for mounting the second LED chip 224b thereon. Specifically, the end surface thereof is higher than the cup 225a of the first mount lead 225.

In view of the above, the use of LED chips disposed at different plane in a single LED package may allow the hollow tube body to be dimensioned and configured to permit insertion into a nostril of a treatment subject, since the occupied cross-section area is thus decreased. Additionally, the second LED chip 224b can be located more near the sidewall of the hollow tube body for easily heating. Hence, a patient could feel comfortable when the hollow tube body touching the internal surface of his nostril such as a rhinitis-afflicted region is warmer.

While the invention has been described by way of example and in terms of the preferred embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A light therapy device, comprising:
   a control unit;
   a pair of hollow tube bodies, each having a central longitudinal axis, being dimensioned and configured to permit insertion into a pair of nostrils of a treatment subject;
   a pair of holders, disposed under the pair of nostrils, sized to receive the pair of hollow tube bodies for clamping the pair of hollow tube bodies to adjacent inner walls of the pair of nostrils;
   a single light emitting diode package, disposed within each of the hollow tube body, comprising:
      a first LED chip as a first light source controlled by the control unit; and
      a second LED chip as a second light source controlled by the control unit,
      wherein the first LED chip only emitting non-coherent light radiation having a narrow band-width centered at a single red light wavelength suitable for rhinitis treatment, is located along the central longitudinal axis of the hollow tube body; and the second LED chip only emitting non-coherent light radiation having a narrow band-width centered at a single infrared light wavelength suitable for heating the hollow tube body, is located a predetermined distance away from the central longitudinal axis thereof and nearer a sidewall of the hollow tube body than the first LED chip;
      wherein the red light wavelength is in a range of about 630 nm to about 660 nm and the infrared light wavelength is in a range of about 920 nm to about 960 nm;
      a first mount lead for mounting the first LED chip aligning the central longitudinal axis of the hollow tube body; and
      a second mount lead for mounting the second LED chip, disposed adjacent an inner wall of the package;
   an inner support tube body disposed within the hollow tube body for supporting the single light emitting diode package, wherein the inner support tube body is opaque and the hollow tube body is transparent; and
   a wider bottom portion, extending from the inner support tube body, wherein the hollow tube body is securely inserted into the wider bottom portion in a detachable form.

2. A light therapy device, comprising:
   a control unit;
   a pair of hollow tube bodies, each having a central longitudinal axis, being dimensioned and configured to permit insertion into a pair of nostrils of a treatment subject;
   a pair of holders, disposed under the pair of nostrils, sized to receive the pair of hollow tube bodies for clamping the pair of hollow tube bodies to adjacent inner walls of the pair of nostrils;
   a single light emitting diode package, disposed within each of the hollow tube body, comprising:
      a first LED chip as a first light source controlled by the control unit; and
      a second LED chip as a second light source controlled by the control unit,
      wherein the first LED chip only emitting non-coherent light radiation having a narrow band-width centered at a single red light wavelength suitable for rhinitis treatment, is located along the central longitudinal axis of the hollow tube body; and the second LED chip only emitting non-coherent light radiation having a narrow band-width centered at a single infrared light wavelength suitable for heating the hollow tube body, is located a predetermined distance away from the central longitudinal axis thereof and nearer a sidewall of the hollow tube body than the first LED chip;
      wherein the red light wavelength is in a range of about 630 nm to about 660 nm and the infrared light wavelength is in a range of about 920 nm to about 960 nm;
      a first mount lead for mounting the first LED chip aligning the central longitudinal axis of the hollow tube body; and
      a second mount lead for mounting the second LED chip, disposed adjacent an inner wall of the package;
   an inner support tube body disposed within the hollow tube body for supporting the single light emitting diode package, wherein the inner support tube body is opaque and the hollow tube body is transparent; and
   a wider bottom portion, extending from the inner support tube body, wherein the hollow tube body is securely inserted into the wider bottom portion in a detachable form;
   wherein the first mount lead further comprises a cup for accommodating the first LED chip; and the second mount lead comprises an end surface higher than the cup of the first mount lead for mounting the second LED chip.

3. The light therapy device as recited in claim 1 wherein the light emitting diode package is powered and controlled, via wires, by the control unit.

4. The light therapy device as recited in claim 3 wherein the wires pass through the inner support tube body.

5. The light therapy device as recited in claim 1 wherein the red light wavelength is about 652 nm and the infrared light wavelength is about 940 nm.

* * * * *